US011857282B2

(12) United States Patent
Huang et al.

(10) Patent No.: US 11,857,282 B2
(45) Date of Patent: Jan. 2, 2024

(54) MULTI-SEGMENT ROTATION ROBOTIC ARM

(71) Applicants: Han-I Huang, Taipei (TW); Hung-Jen Lin, Kinmen County (TW)

(72) Inventors: Han-I Huang, Taipei (TW); Hung-Jen Lin, Kinmen County (TW)

( * ) Notice: Subject to any disclaimer, the term of this patent is extended or adjusted under 35 U.S.C. 154(b) by 311 days.

(21) Appl. No.: 17/321,552

(22) Filed: May 17, 2021

(65) Prior Publication Data

US 2021/0361368 A1 Nov. 25, 2021

(30) Foreign Application Priority Data

May 19, 2020 (TW) .................................. 109116529

(51) Int. Cl.
*A61B 34/30* (2016.01)
*A61B 34/00* (2016.01)
*B25J 9/04* (2006.01)

(52) U.S. Cl.
CPC .............. *A61B 34/70* (2016.02); *A61B 34/30* (2016.02); *B25J 9/04* (2013.01); *A61B 2034/301* (2016.02); *A61B 2034/302* (2016.02)

(58) Field of Classification Search
CPC ....... B25J 9/065; B25J 17/0291; A61B 34/70; A61B 34/30; A61B 2034/301; A61B 2034/302; A61B 2034/303; A61B 2017/00314
See application file for complete search history.

(56) References Cited

U.S. PATENT DOCUMENTS

| | | | | |
|---|---|---|---|---|
| 4,990,050 A | * | 2/1991 | Tsuge | F16D 3/16 901/29 |
| 6,796,203 B2 | * | 9/2004 | Dubrowskij | A61B 17/00234 74/423 |
| 6,871,563 B2 | * | 3/2005 | Choset | B25J 17/0275 901/29 |
| 6,976,401 B2 | * | 12/2005 | Okamoto | B25J 17/0291 74/490.03 |
| 9,550,299 B2 | * | 1/2017 | Wolf | B25J 17/00 |
| 2004/0129103 A1 | * | 7/2004 | Kamon | B25J 17/025 74/490.01 |

(Continued)

FOREIGN PATENT DOCUMENTS

| | | | | |
|---|---|---|---|---|
| CN | 107116543 A | * | 9/2017 | ............ B25J 9/065 |
| CN | 208209204 U | * | 12/2018 | |
| WO | WO-2019240587 A1 | * | 12/2019 | ............ A61G 5/10 |

*Primary Examiner* — Bobby Rushing, Jr.
(74) *Attorney, Agent, or Firm* — WPAT, P.C

(57) ABSTRACT

Provided is a multi-segment rotation robotic arm which contains a plurality of concatenated robotic arm segments which can rotate 360 degrees along an adjacent oblique section thereof. Any one of the concatenated robotic arm segments of the multi-segment rotation robotic arm can be arbitrarily concatenate in accordance with use requirements. When the concatenated robotic arm segments rotate relatively, they can rotate 360 degrees without affecting the electric supply, and can also reduce the volume increase by rotated joints. Therefore, the multi-segment rotation robotic arm of the present invention can effectively adapt to complex and tortuous spaces in the body cavity to reduce the possibility of expanding the opening of the minimally invasive surgery and causing damage to organs or tissues in the body cavity.

10 Claims, 11 Drawing Sheets

(56) References Cited

U.S. PATENT DOCUMENTS

2004/0149064 A1\* 8/2004 Narita .................... B25J 9/06
   74/490.03
2018/0243927 A1\* 8/2018 Dufau ................... B25J 9/1045
2019/0070726 A1\* 3/2019 Bilsky ................... B23B 39/14

\* cited by examiner

MULTI-SEGMENT ROTATION ROBOTIC ARM

CROSS-REFERENCE TO RELATED APPLICATION

This application claims priority of Taiwan patent application No. 109116529, filed on May 19, 2020, the content of which are incorporated herein in its entirety by reference.

BACKGROUND OF THE INVENTION

1. Field of the Invention

The present invention relates to a multi-segment rotation robotic arm, and more particularly to a multi-segment rotation robotic arm with a plurality of concatenated robotic arm segments, which can rotate 360 degrees along an adjacent oblique section thereof, for surgical operations and medical endoscopy.

2. The Prior Art

With the advancement of medical technology, new surgical techniques are constantly being introduced. The surgical techniques which enable patients to obtain rapid, low-risk, and short recovery time have always been the goals pursued by the medical community, and minimally invasive surgery, which has been popular in recent years, is one of them. In minimally invasive surgery, abdominal endoscopic surgery and pelvic endoscopic surgery are the most common, which mainly uses micro-endoscope imaging technology to present the surgical field of vision, and uses micro-surgical instruments to perform the surgery, so that the patient can be performed the surgery without forming a huge wound, which not only greatly reduces the patient's blood loss, but also can heal quickly because of the small wound.

In the current endoscopy, optical fibers are used, and the optical fibers are slowly inserted into the throat, intestines, and other places by manual manners for internal observation. However, because the optical fiber is a flexible tube, it is difficult to apply force, conduct force, and accurately guide, which makes it very difficult to operate the optical fiber when it is placed in the throat, intestine, and other places. Therefore, if an easy-to-operate endoscopic instrument can be provided for endoscopic inspection equipment, it will greatly reduce the difficulty of endoscopic inspection and lay the foundation for future automated endoscopic inspections.

On the other hand, since the limitation of incisions in minimally invasive surgery, when inserting instruments, which are required for minimally invasive surgery, into the body, it is necessary to prevent the wound from expanding the wound due to the swinging process of the surgical instrument, otherwise the spirit and effect of the minimally invasive surgery will be lost. Therefore, the design of minimally invasive surgical instruments usually has multiple degrees of freedom, and it is necessary to be able to accurately control the swing direction and angle of the micro-surgical instruments, so that the surgical instruments on the surgical instruments can be smoothly inserted into the body.

However, the currently used robotic arms usually have a considerable volume. Therefore, for a relatively limited surgical space, if the volume of the robotic arm can be reduced, it will be beneficial to the space configuration of the minimally invasive surgery system and can avoid interference to the operation of medical staff; in addition, most of the movements of the currently used robotic arms require complex mathematical operations, so it is more likely that the robotic arm will accidentally touch non-surgical tissues due to calculation errors, which may cause safety concerns. The joints of such robotic arms can usually only rotate to a limited extent, and these joints will increase the volume of the robotic arms, making the currently used robotic arms not suitable for curved and complex internal spaces.

Furthermore, the entire minimally invasive surgery system usually includes many robotic arms to install many micro-surgical instruments with different functions, and the actions of these robotic arms will restrict each other, and the devices that drive the robotic arms to rotate will also be limited by space constraints, thereby restricting the rotation angle of each robotic arm. Therefore, the robotic arm can only drive micro-surgical instruments to move within a fairly limited working range.

In summary, in order to increase the safety of minimally invasive surgery and improve the efficiency and accuracy of minimally invasive surgery, it is really necessary to develop a robotic arm that is easy to operate, small in size, and large in mobility of joint.

SUMMARY OF THE INVENTION

To solve the foregoing problem, one objective of the present invention is to provide a multi-segment rotation robotic arm, comprising: a plurality of concatenated robotic arm segments; wherein any one of the concatenated robotic arm segments is an elliptical cylinder having an oblique section at each end, and the oblique section is a circle; and a pivoting structure and a driving device are located between two of the concatenated robotic arm segments, wherein, the pivoting structure is located between an adjacent oblique section of the two of the concatenated robotic arm segments, and the driving device is used to drive the pivoting structure so that the two of the concatenated robotic arm segments move relatively to each other along the adjacent oblique section.

In one embodiment of the present invention, the elliptical cylinder of the robotic arm segment has at least one hollow structure which penetrates both ends of the robotic arm segment.

In one embodiment of the present invention, the driving device comprises: an electric motor, an electrical conduction element for conducting electricity to the electric motor, and/or a battery for providing electricity to the electric motor; wherein, the electric motor is installed at one end of the two of the concatenated robotic arm segments for driving the pivoting structure, and the electrical conductive element and/or the battery is arranged in the hollow structure.

In one embodiment of the present invention, a conductive ring combination is arranged at the adjacent oblique section of the two of the concatenated robotic arm segments, so that the electrical conduction element of the concatenated robotic arm segments is electrically connected by the conductive ring combination to conduct electricity.

In one embodiment of the present invention, the driving device further comprises a signal receiving module, an electric motor, and a signal processing module; wherein, the signal processing module is electrically connected to the signal receiving module and the electric motor.

In one embodiment of the present invention, the signal receiving module receives a control signal and transmits the control signal to the signal processing module, and the signal processing module receives the control signal to calculate a rotation angle.

In one embodiment of the present invention, the signal processing module controls the rotation of the electric motor according to the rotation angle and drives the two of the concatenated robotic arm segments to perform relative rotation at the rotation angle along the adjacent oblique sections.

In one embodiment of the present invention, a terminal of the multi-segment rotation robotic arm further comprises a signal receiving module, an instrument device, and a signal processing module; wherein the signal processing module is electrically connected to the signal receiving module and the instrument device.

In one embodiment of the present invention, the signal receiving module receives a control signal and transmits the control signal to the signal processing module, and the signal processing module receives the control signal to generate an operation instruction.

In one embodiment of the present invention, the signal processing module controls an operation of the instrument device according to the operation instruction.

In the multi-segment rotation robotic arm of the present invention, the robotic arm segment has a circle with the same diameter at both ends (i.e. the oblique section), so that after the robotic arm segment of the present invention is concatenated in series, the robotic arm segments concatenated in series can completely perform relative rotations of up to 360 degrees along the adjacent oblique sections of the two of the concatenated robotic arm segments without extra volume. In addition, since the hollow structure penetrating both ends of the robotic arm segment takes the rotation center of the pivoting structure as the center point of itself, objects placed in the hollow structure would not be affected when the robotic arm segment concatenated in series perform relative rotational movement.

Furthermore, in the multi-segment rotation robotic arm of the present invention, each concatenated robotic arm segment of the robotic arm is concatenated in series with the conductive ring combination, so that it is only necessary to connect an external electric supply to an terminal of the robotic arm segment (usually the initial one) of the multi-segment rotation robotic arm of the present invention for supplying electricity to the entire multi-segment rotation robotic arm; and since the conductive ring combination is a circular metal ring, the two robotic arm segments connected in series can freely rotate 360 degrees without affecting the conduction of electricity after the robotic arm segments are concatenated in series; or, each of the robotic arm segments concatenated in series has a battery to independently provide electricity for a single robotic arm segment, so that the rotation of the robotic arm segment would not affect the conduction of electricity.

In addition, in the multi-segment rotation robotic arm of the present invention, each robotic arm segment comprises an independent signal receiving module and a signal processing module, and the terminal of the robotic arm segment can further comprises an instrument device, so that each robotic arm segment can be independently controlled to reduce each controlled unit and to improve the overall mobility and accuracy of the multi-segment rotation robotic arm of the present invention.

Therefore, the multi-segment rotation robotic arm of the present invention can arbitrarily concatenate a plurality of the robotic arm segments of the present invention in series according to the use requirements, and the concatenating way of the robotic arm segments enables them to rotate 360 degrees along the oblique section of each other when they rotate relatively to each other, and the electric supply will not be affected by the rotation at all, so as to overcome the limitation of the joint rotation angle of the conventional robotic arm in the art of the present invention, and to reduce the volume increase by rotated joints, so the multi-segment rotation robotic arm of the present invention can be more effectively used in minimally invasive surgery with limited space configuration. Specifically, the multi-segment rotation robotic arm of the present invention can effectively adapt to the complex and tortuous space in the body cavity to reduce the possibility of expanding the opening of the minimally invasive surgery and causing damage to organs or tissues in the body cavity. Moreover, because each robotic arm segment of the multi-segment rotation robotic arm of the present invention can be independently controlled, this method of reducing the control unit enables the multi-segment rotation robotic arm of the present invention to adapt to the environment in terms of mobility and accuracy.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

According to the present invention, the operating procedures and parameter conditions of a joint are within the professional literacy and routine techniques of those having ordinary skill in the art.

According to the present invention, the operating procedures and parameter conditions of a motor are within the professional literacy and routine techniques of those having ordinary skill in the art; and the motor used in the present invention can be any of the conventionally used motor types in the technical art of the present invention.

According to the embodiment of the present invention, the materials of the robotic arm, the sleeve of the robotic arm, or an outer protective film of the robotic arm is, but not limited to, a bio-compatible rubber, a silicone, a latex, a plastic (e.g. PVC, PU, PP, PE, PTFE, etc.), a stainless steel, a plastic steel, a metal (e.g. Titanium alloy or Titanium six aluminum four vanadium (Ti6Al4V)), a composite material, a wood, or other materials.

According to the embodiments of the present invention, the operating procedures and parameter conditions related to the wireless connection are within the professional literacy and routine techniques of those having ordinary skill in the art; and the wireless connection used in the present invention can be any of the conventionally used types in the art of the present invention, which can be but not limited to infrared, Bluetooth, ZigBee, ANT, Wi-Fi, etc.

Figure 1:
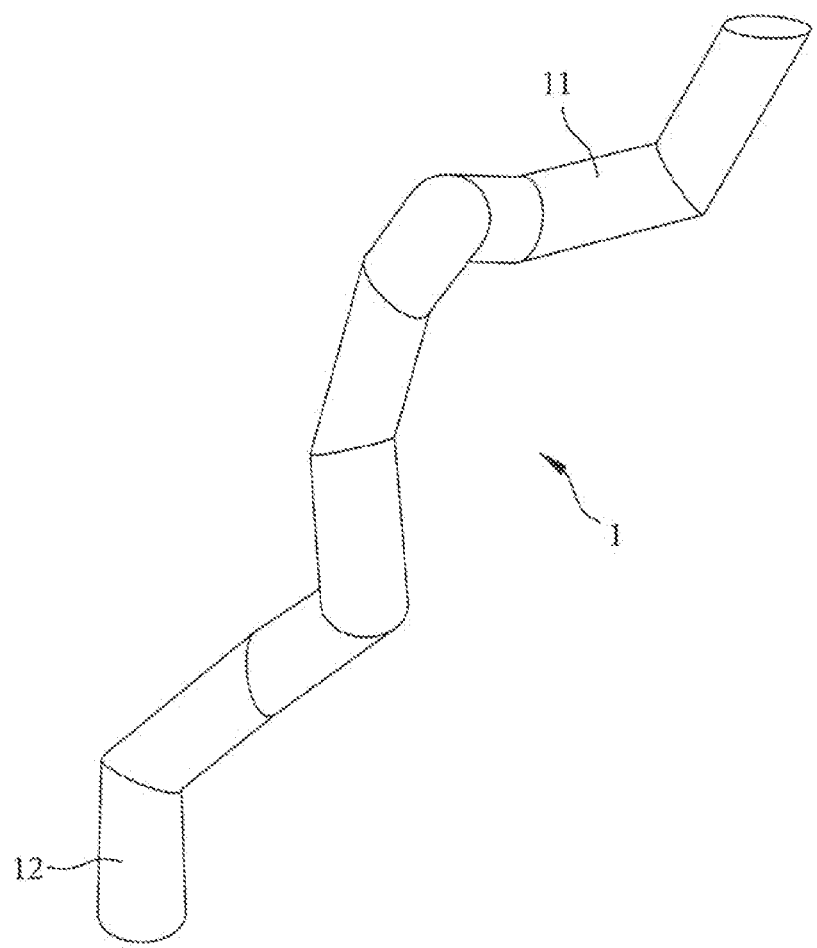
FIG. 1 shows a schematic view of the multi-segment rotation robotic arm according to an embodiment of the present invention.

Please refer to FIG. 1, which is the schematic view of the multi-segment rotation robotic arm 1 of the present invention. The multi-segment rotation robotic arm 1 comprises a plurality of concatenated robotic arm segments 11 and a terminal robotic arm segment 12 located at a terminal of the multi-segment rotation robotic arm 1. Wherein, the concatenated robotic arm segment 11 has a front end and a rear end, and the two of the serially concatenated robotic arm segments 11 or the terminal robotic arm segment 12 can rotate along the adjacent oblique section; and the front end of the terminal robotic arm segment 12 can be further disposed with a clamp or a lighting source device.

Figure 2A:
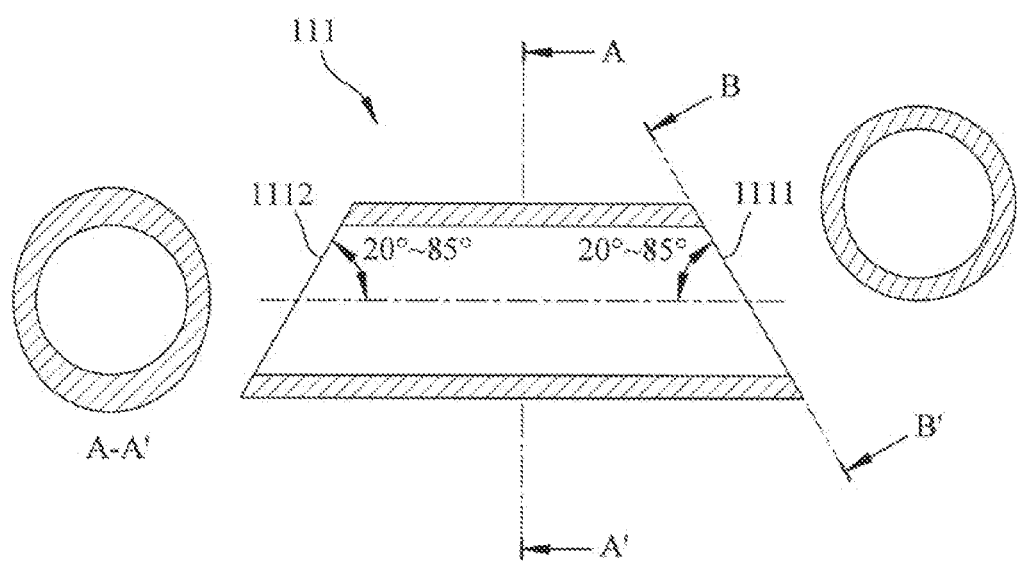
FIG. 2A shows a cross-sectional view of the sleeve of the multi-segment rotation robotic arm of one embodiment of the present invention.
Figure 2B:
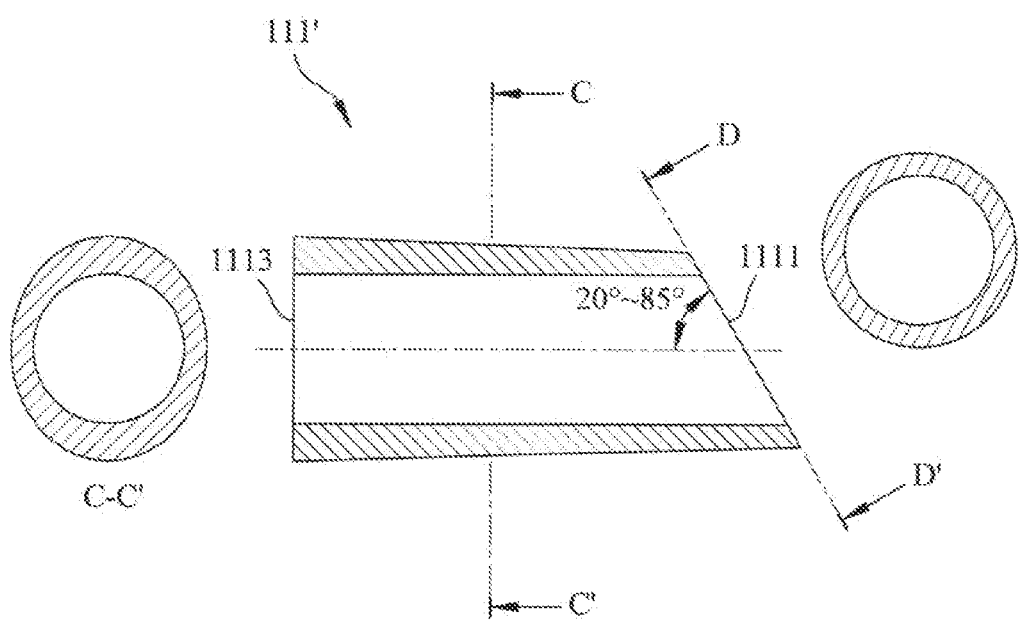
FIG. 2B shows a cross-sectional view of the sleeve of the multi-segment rotation robotic arm of another embodiment of the present invention.

Please refer to FIGS. 2A and 2B, which show the cross-sectional view of the different sleeves of the multi-segment rotation robotic arm of the present invention, respectively. FIG. 2A is the sleeve of one embodiment of the present invention, and the sleeve 111 is applied to the concatenated robotic arm segment 11. The sleeve 111 is an elliptical cylinder, as shown in the section A-A', and the two ends of the sleeve 111 are a front end oblique section 1111 near the front end and a rear end oblique section 1112 near the rear end respectively. The internal structure of the sleeve 111 has a hollow structure penetrating the front end oblique section 1111 and the rear end oblique section 1112; wherein, the front end oblique section 1111 and the rear end oblique section 1112 are both a circle (as shown in section B-B'), and the front end oblique section 1111 and the rear end oblique section 1112 respectively form an acute angle of 20-85 degrees with the longitudinal axis of the elliptical cylinder of the sleeve 111, and the acute angle is preferably 40-80 degrees.

FIG. 2B is the sleeve of another embodiment of the present invention, and the sleeve 111' is applied to the terminal robotic arm segment 12. The sleeve 111' is also an elliptical cylinder, as shown in the section C-C', and the two ends of the sleeve 111' are a front end oblique section 1111 near the front end and a vertical oblique section 1113 near the rear end respectively; wherein, the front end oblique section 1111 is a circle (as shown in section D-D'), which forms an acute angle of 20-85 degrees with the longitudinal axis of the elliptical cylinder of the sleeve 111', and the acute angle is preferably 40-80 degrees. The vertical oblique section 1113 at the rear end (as shown in section C-C') forms a vertical angle with the longitudinal axis, so that the vertical oblique section 1113 forms a platform for further disposition and/or connection of other instruments or devices on the platform.

Figure 3A:
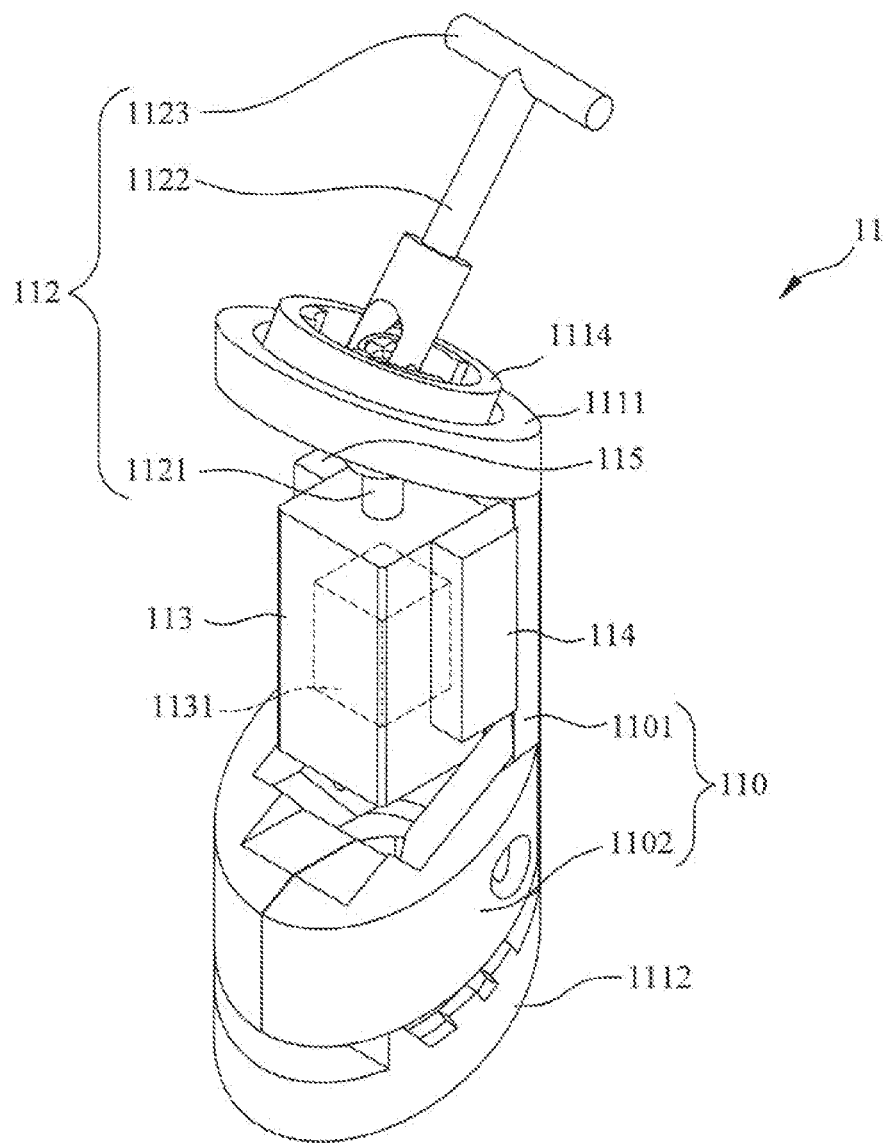
FIG. 3A shows a schematic view of a robotic arm segment, which comprises a supporting device, the pivoting structure, the driving device, the signal receiving module, and the signal processing module according to one embodiment of the present invention.
Figure 3B:
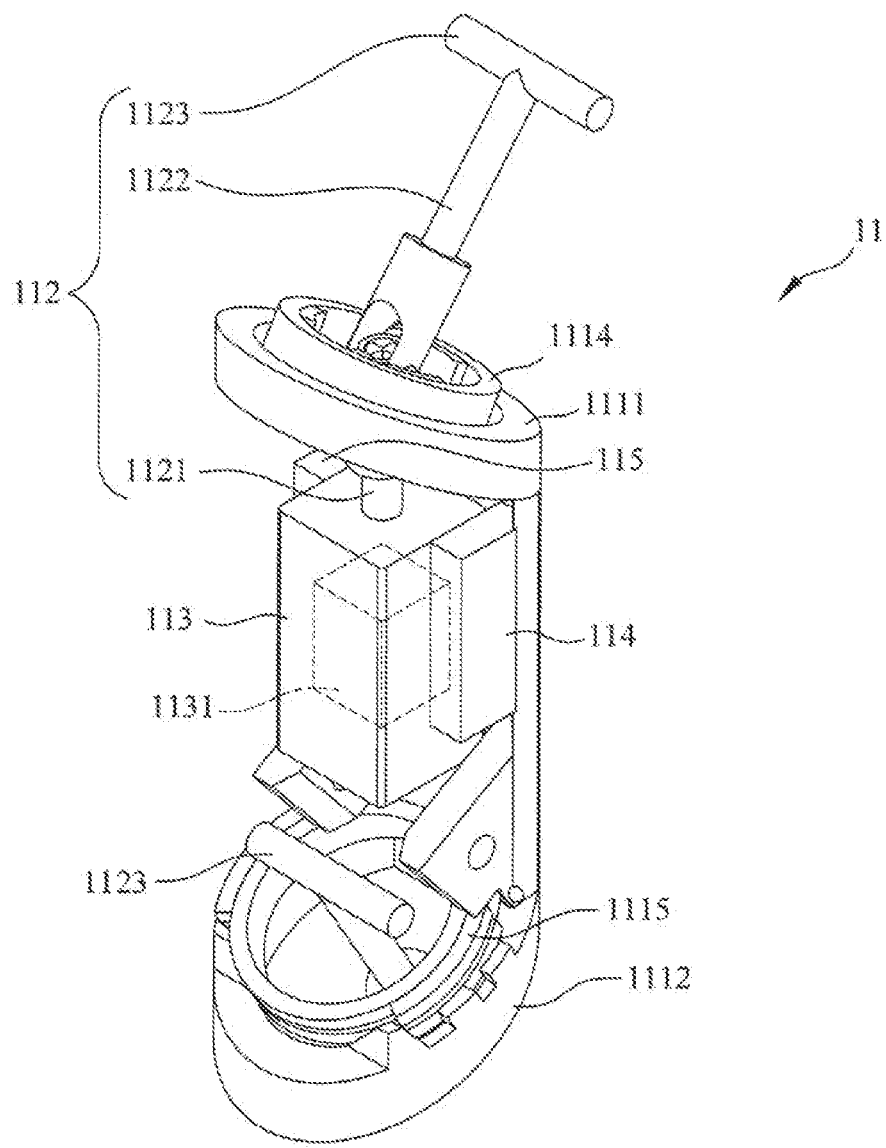
FIG. 3B shows a schematic view of removing the supporting base in FIG. 3A.

In one embodiment of the multi-segment rotation robotic arm of the present invention, referring to FIGS. 3A and 3B, the hollow structure penetrates both ends of the sleeve 111, and a supporting device 110, a pivoting structure 112, and a driving device 113 for driving the pivoting structure are disposed in the hollow structure. The supporting device 110 is fixed in the sleeve 111 to fix and support the pivoting structure 112, the driving device 113, the signal receiving module 114, and the signal processing module 115 in the concatenated robotic arm segment 11. The supporting device 110 comprises a supporting frame 1101 and a supporting base 1102, wherein the supporting frame 1101 penetrates the front and rear ends of the concatenated robotic arm segment 11, and the supporting base 1102 is fixed at the rear end oblique section 1112 of the sleeve 111.

The pivoting structure 112 is located between the front end oblique section 1111 and the rear end oblique section 1112 adjacent to the two serially concatenated robotic arm segments 11, and the driving device 113 is disposed inside the hollow structure of the sleeve 111 of the concatenated robotic arm segment 11 to drive the pivoting structure 112, so that the two serially concatenated robotic arm segments 11 move relatively to each other along the adjacent oblique sections; wherein a circular flange 1114 is formed on the rear end oblique section 1112, and a circular groove 1115 is formed on the front end oblique section 1111. When the front end oblique section 1111 and the rear end oblique section 1112 are adjacent to each other, the circular flange 1114 and the circular groove 1115 cooperate with each other to keep the adjacent oblique sections rotating relatively to each other, and to prevent the deviation between the two oblique sections.

The driving device 113 in the concatenated robotic arm segment 11 of the present invention further comprises a signal receiving module 114 and a signal processing module 115; wherein the signal receiving module 114 is wirelessly connected to a remote control device, and the signal processing module 115 is electrically connected to the signal receiving module 114 and the motor 1131; wherein the signal receiving module 114 wirelessly receives a motor control signal from the remote control device, and then sends the motor control signal 1141 to the signal processing module 115; and after receiving the motor control signal 1141, the signal processing module 115 calculates a rotation angle; and then, the signal processing module 115 controls the motor 1131 to perform a corresponding rotation according to the rotation angle, and drives the two serially concatenated robotic arm segments 11 to perform relative rotation at the rotation angle along the adjacent oblique sections.

Figure 4:
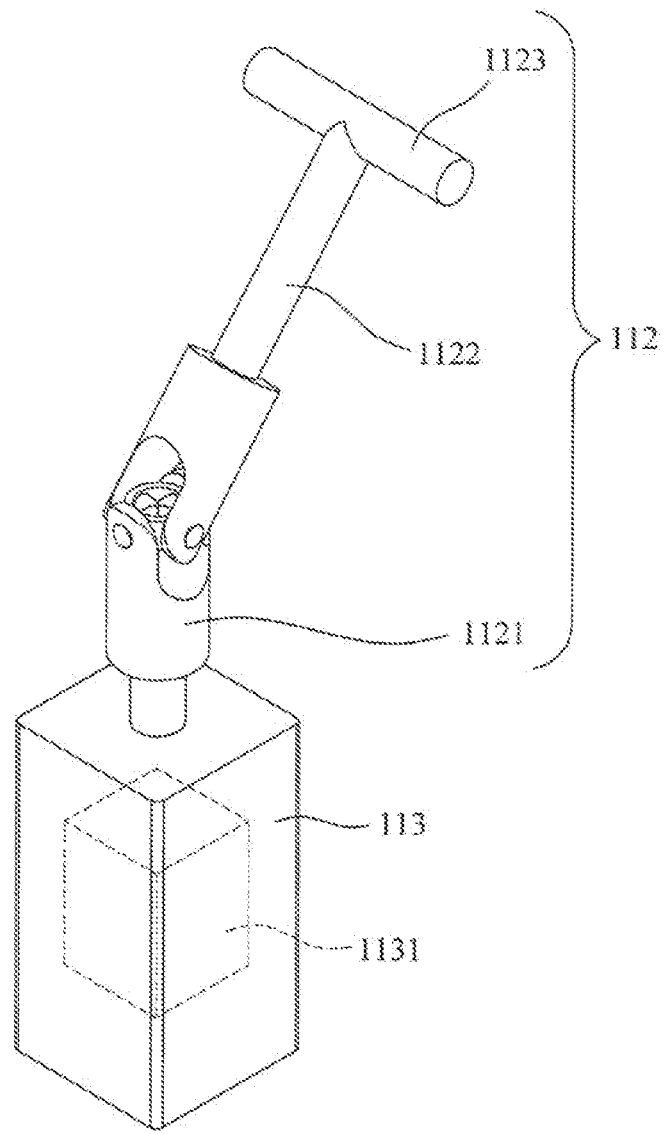
FIG. 4 shows a schematic view of a pivoting structure and a driving device of the multi-segment rotation robotic arm according to an embodiment of the present invention.

Please continue to refer to FIG. 4, the pivoting structure 112 comprises: a front end joint 1121, which is near the front end oblique section 1111; a rear end joint 1122, which is near the rear end oblique section 1112 of the next concatenated robotic arm segment 11; and a T-shaped structure 1123, which is extending from the rear end joint 1122; wherein the front end joint 1121 and the rear end joint 1122 are pivotally coupled by a universal joint, and a pivoting angle maintained by the front end joint 1121 and the rear end joint 1122 is the angle maintained along the two oblique sections of the two serially concatenated robotic arm segments 11. The motor 1131 is installed in the hollow structure near the front end of the concatenated robotic arm segment 11, and a rotating shaft of the motor 1131 is coupled to the front end joint 1121 to rotate the front end joint 1121 to drive the rotation of the rear end joint 1122. In addition, the T-shaped structure 1123 extended from the rear end joint 1122 is connected to the supporting base 1102 which is at the rear end of the concatenated robotic arm segment 11, so that the concatenated robotic arm segment 11 concatenated in series follows the rotation of the pivoting structure 112 to rotate.

In another embodiment of the present invention, the terminal robotic arm segment 12 is the first robotic arm segment of the multi-segment rotation robotic arm 1, and the front end oblique section 1111 of the terminal robotic arm segment 12 and the rear end oblique section 1112 of the concatenated robotic arm segment 11 are adjacent to each other in the aforementioned manner, and the hollow structure of the sleeve 111' and the hollow structure of the sleeve 111 communicate with each other.

In another embodiment of the present invention, the terminal robotic arm segment 12 is the last robotic arm segment of the multi-segment rotation robotic arm 1, and the front end oblique section 1111 of the terminal robotic arm segment 12 and the front end oblique section 1111 of the concatenated robotic arm segment 11 are adjacent to each other in the aforementioned manner, and the hollow structure of the sleeve 111' and the hollow structure of the sleeve 111 communicate with each other; wherein, the front end oblique section 1113 of the terminal robotic arm segment 12 can be, but not limited to, a structure which has installed a specific instrument device, such as a clamp, so that the terminal robotic arm segment 12 forms a specific unit body, which can be replace according to the use requirements.

In other embodiments of the present invention, the entire combination of pivoting structure 112 and the driving device 113 may be a piezoelectric motor, more specifically, may be an ultrasonic piezoelectric motor. For example, the driving device 113 is a driving part of the piezoelectric motor and is arranged in the concatenated robotic arm segment 11, and the pivoting structure 112 is a sliding rail part of the piezoelectric motor and is arranged in the next concatenated robotic arm segment 11. In this way, when the driving part of the concatenated robotic arm segment 11 is operating, the slide rail part of the next concatenated robotic arm segment 11 can be driven to rotate.

Figure 5:
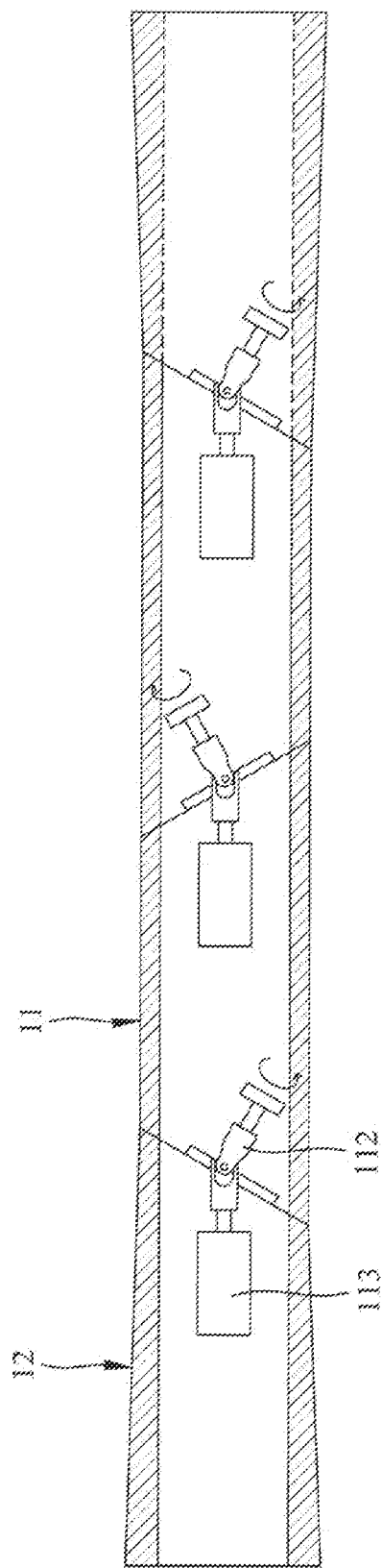
FIG. 5 shows a cross-sectional view of the robotic arm segment concatenated in series according to an embodiment of the present invention.

Please refer to FIG. 5, the multi-segment rotation robotic arm 1 of the present invention can arbitrarily concatenate a plurality of the concatenated robotic arm segments 11 of the present invention in series according to the use requirements, and the concatenating way of the concatenated robotic arm segments 11 enables themselves to rotate 360 degrees along the oblique section of each other when they rotate relatively to each other, and the electric supply will not be affected by the rotation at all, so as to reduce the volume increase by rotated joints, so the multi-segment rotation robotic arm 1 of the present invention can be more effectively adapt to the complex and tortuous space in the body cavity to reduce the possibility of expanding the opening of the minimally invasive surgery and causing damage to organs or tissues in the body cavity, and because each concatenated robotic arm segment 11 of the multi-segment rotation robotic arm 1 of the present invention can be independently controlled, the multi-segment rotation robotic arm 1 of the present invention to adapt to the environment in terms of mobility and accuracy.

Figure 6:
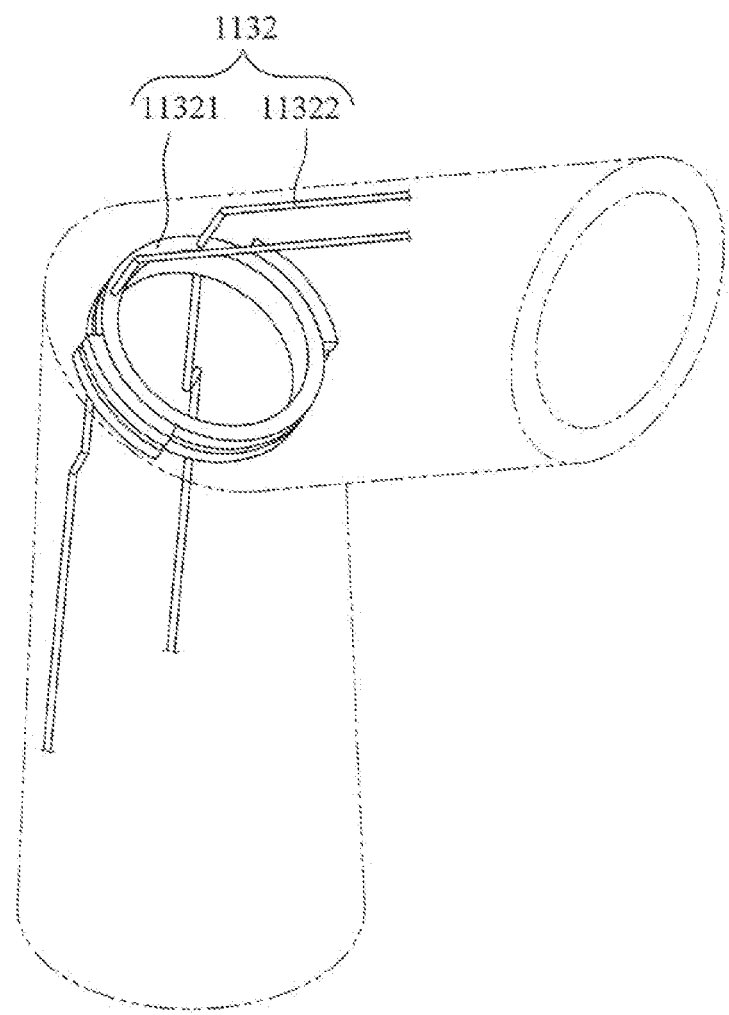
FIG. 6 shows a schematic view of electrical conductive element of the multi-segment rotation robotic arm according to another embodiment of the present invention.

Referring to FIG. 6, in another embodiment of the present invention, the driving device 113 comprises: an electric motor 1131, and an electrical conductive element 1132 electrically connected to the motor 1131. The electrical conductive element 1132 is a conductive ring combination 11321 and a conductive wire combination 11322, wherein the conductive wire combination 11322 electrically connects the conductive ring combination 11321 with the driving device 113, the signal receiving module 114, and the signal processing module 115 respectively; and the conductive ring combination 11321 is arranged on the circular flange 1114 and the circular groove 1115 of the concatenated robotic arm segment 11 respectively; thus, when the concatenated robotic arm segment 11 is concatenated in series, the two of the concatenated robotic arm segments 11 are electrically connected by the conductive ring combination 11321 to conduct electricity; wherein the conductive ring combination 11321 is a circular metal ring, so that the rotation of the robotic arm segments concatenated in series would not affect the conduction of electricity.

In another embodiment of the present invention, not shown in the FIGs, the electrical conductive element 1132 is a battery, and the battery is disposed in the driving device 113 and electrically connected to the electric motor 1131 to independently provide electricity for the driving device 113 of a single concatenated robotic arm segment 11, so that the rotation of the robotic arm segments concatenated in series would not affect the conduction of electricity.

Figure 7:
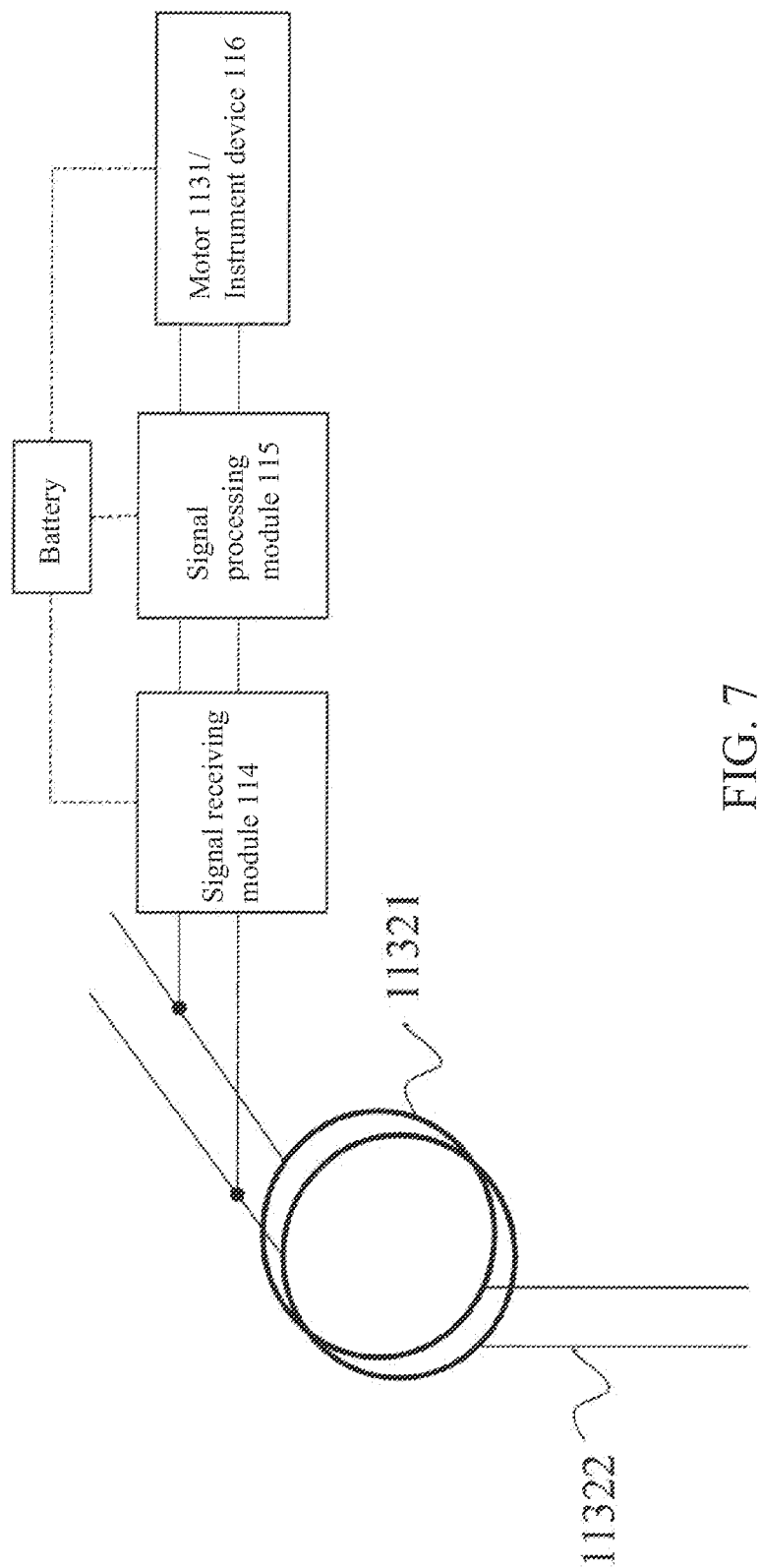
FIG. 7 shows a schematic diagram of the transmission and reception of electricity and signals of the multi-segment rotation robotic arm according to another embodiment of the present invention.

In an embodiment of the present invention, the driving device 113 further comprises a receiving module 114, an electric motor 1131/an instrument device 116, and a signal processing module 115, wherein the signal receiving module 114 receives a control signal and sends the control signal to the signal processing module 115, and the signal processing module 115 receives the control signal to calculate a rotation angle/an operation instruction; please refer to FIG. 7 for the transmission and reception methods of electricity and signals, including, but not limited to, any of the 4 methods mentioned below:

(1) The conductive ring combination 11321 transmits electricity to the signal receiving module 114, the signal processing module 115, and the electric motor 1131/the instrument device 116, wherein the signal receiving module 114 wirelessly receives the control signal and sends it to the signal processing module 115 to control the electric motor 1131/the instrument device 116 without using batteries;

(2) The conductive ring combination 11321 transmits electricity and carrier control signals, and the electricity is transmitted to the signal receiving module 114, the signal processing module 115, and the electric motor 1131/the instrument device 116, wherein the signal receiving module 114 receives and carries the control signal by wire, and transmits it to the signal processing module 115 to control the electric motor 1131/the instrument device 116 without using batteries. In addition, the number of the rings of the conductive ring combination 11321 and the conductive wire combination 11322 is not limited to two. In other embodiments of the present invention, the number of the rings may be more than two, such as four rings, six rings, etc., and each ring can be electrically connected to the signal receiving module 114, the signal processing module 115 and the electric motor 1131/the instrument device 116, so that different signals can be transmitted to the electric motor 1131/the instrument device 116 through different rings, and then the electric motor 1131 rotates a predetermined angle or the instrument device 116 performs an action;

(3) The conductive ring combination 11321 transmits the control signal, and further comprises the battery to provide electricity to the signal receiving module 114, the signal processing module 115, and the electric motor 1131/the instrument device 116; wherein the signal receiving module 114 receives the control signal by wire and transmits it to the signal processing module 115 to control the electric motor 1131/the instrument device 116;

(4) The battery provides electricity to the signal receiving module 114, the signal processing module 115, and the electric motor 1131/the instrument device 116; wherein, the signal receiving module 114 wirelessly receives the control signal and transmits it to the signal processing module 115 to control the electric motor 1131/the instrument device 116.

The robotic arm of the present invention can be further equipped with an instrument device for microsurgery, wherein the accessory instrument for surgery is a commonly used instrument for those with ordinary skill in the art of the present invention, which can be, but not limited to, a scissors, a clamp, a hemostat, a hook, an electrosurgical unit, or a harmonic scalpel, etc.

Figure 8:
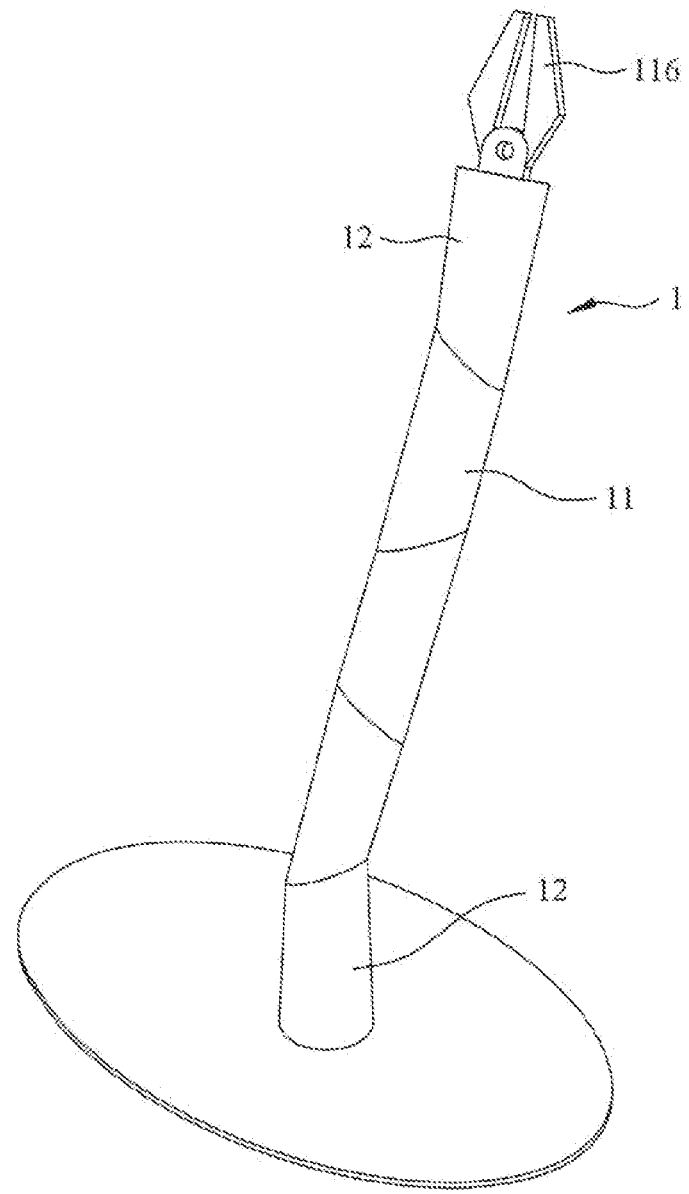
FIG. 8 shows a schematic diagram of an instrument device disposed at the terminal of the multi-segment rotation robotic arm, wherein the instrument device is a clamp according to an embodiment of the present invention.

Referring to FIG. 8, in an embodiment of the present invention, the terminal robotic arm segment 12 of the multi-segment rotation robotic arm 1 further comprises an instrument device 116; wherein the signal receiving module 114 is wirelessly connected to a remote control device, and the signal processing module 115 is electrically connected to the signal receiving module 114 and the instrument device 116; wherein the signal receiving module 114 wirelessly receives an instrument device control signal from the remote control device, and then transmits the instrument device control signal to the signal processing module 115; and after receiving the instrument device control signal, the signal processing module 115 calculates an operation instruction, and then the signal processing module 115 controls the operation of the instrument device 116 according to the operation instruction.

Figure 9:
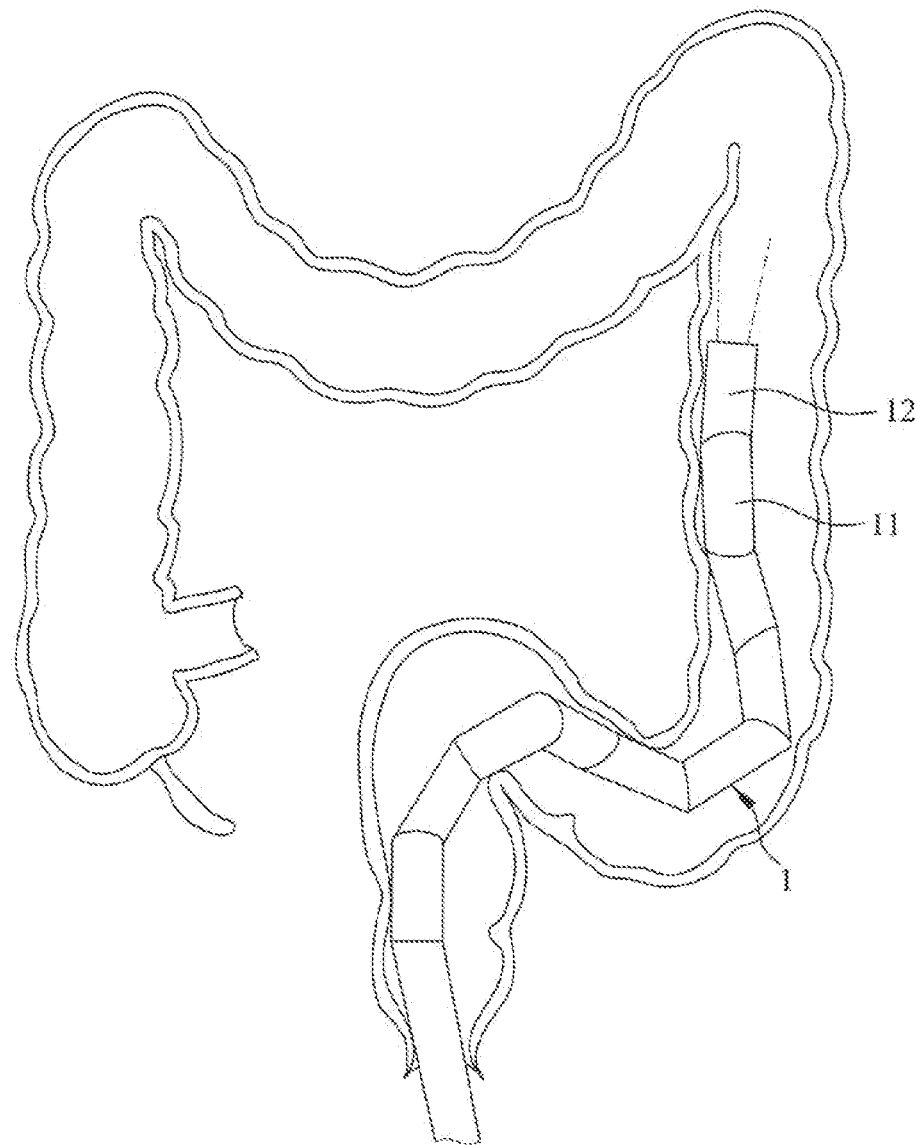
FIG. 9 shows a schematic diagram of a lighting source device disposed at the terminal of the multi-segment rotation robotic arm according to an embodiment of the present invention and used thereof in the intestinal tract.

In one embodiment of the present invention, the robotic arm may further comprise a magnet, or the concatenated robotic arm segment 11 itself is made of magnetic material, so that when performing surgical operations with the robotic arm of the present invention, the positioning of the robotic arm extending into the affected area can be controlled by magnetic force outside or inside of the body, or the weight-bearing capacity of the robotic arm can be increased Referring to FIG. 9, the robotic arm of the present invention may further comprise an image transmission device, a lighting source device, or any combination thereof, which is directly arranged at the front end of the end robotic arm segment of the multi-segment rotation robotic arm 1 of the present invention, i.e. the rear end oblique section 1113 of the terminal robotic arm segment 12, or is arranged in the hollow structure penetrating the concatenated robotic arm segment 11 and the terminal robotic arm segment 12 and extends to the front end of the last robotic arm segment. As shown in FIG. 9, the concatenated robotic arm segment 11 and the terminal robotic arm segment 12 of the present invention can adapt to the complex and tortuous space in the body cavity through multiple different rotation angles to reduce the possibility of expanding the wound and reduce the risk of causing organ and tissue damage in the body cavity.

In addition to being directly used, the multi-segment rotation robotic arm 1 of the present invention can also be used after being coated with a protective film on the outer surface of the multi-segment rotation robotic arm 1, so as to reduce the cleaning burden and failure of the multi-segment rotation robotic arm 1, and can improve safety.

The robotic arm of the present invention can be applied to throat endoscopes, gastrointestinal endoscopes, abdominal endoscopes, thoracic endoscopes, pelvic gun endoscopes and other operations based on common skill in the art of the present invention. It is worth mentioning that the present invention uses a multi-segment rotation robotic arm which belongs to a flexible tube to replace the conventional optical fiber and can be operated by automatic mechanization. In this way, the robotic arm of the present invention can easily apply force and transmit force to move and rotate in places such as the throat and intestines, and adapt to the complex and tortuous space in the body cavity through multiple rotation angles; in addition, the robotic arm of the present invention 1 can also be covered with a layer of intestinal cleansing devices commonly used in the art of the present invention to improve the accuracy and efficiency of cleaning the intestines.

The application of the multi-segment rotation robotic arm 1 of the present invention in laparoscopic endoscopic surgery will be described in detail below; however, those with ordinary skill in the art of the present invention should be able to understand that such detailed descriptions and specific examples for implementing the present invention are only used to illustrate the present invention, and are not intended to limit the scope of the claims of the present invention.

EXAMPLE

The application of the multi-segment rotation robotic arm of the present invention in abdominal endoscopic surgery One embodiment of the present invention is the application of the multi-segment rotation robotic arm 1 in peritoneal endoscopic surgery. After using the conventional art in the art of the present invention to have wounds of abdominal endoscopic surgery and infuse carbon dioxide into the abdominal cavity to open up the space, (1) the multi-segment rotation robotic arm 1 of the present invention in which the instrument device 116 is a clamp, (2) the multi-segment rotation robotic arm 1 of the present invention in which the instrument device 116 is another clamp, and (3) the multi-segment rotation robotic arm 1 of the present invention comprising an image transmission device and a lighting source device are respectively inserted into the body through the open wound. Because the multi-segment rotation robotic arm 1 of the present invention is small in size and has multiple joints which can rotate 360 degrees without affecting the volume of the multi-segment rotation robotic arm 1, so that when the aforementioned (1) to (3) are placed into the abdominal cavity of the patient, the multi-segment rotation robotic arm 1 can adapt to the complex and tortuous space in the body cavity to reduce the possibility of expanding the opening of the minimally invasive surgery and causing damage to organs or tissues in the body cavity.

Then, an erecting platform which can be folded into a small volume can also be placed in the abdominal cavity of the patient through the wound, and because the multi-segment rotation robotic arm 1 of the present invention can further comprise a magnet or have polarity itself, a magnet could be used to properly adjust the position of the abovementioned (1) to (3) and the erecting platform in the abdominal cavity of the patient on the outside of the body, and after the relative distance of the objects is shortened, the erecting platform is spread out and the aforementioned (1) to (3) are combined on the erecting platform to form a complete minimally invasive surgery operation assembly, and, the electric motor control signal or the instrument device control signal is transmitted to the robot arm 1 of the present invention through the remote control device to control the multi-segment rotation robotic arm 1 of the present invention for minimally invasive surgery.

In summary, in the multi-segment rotation robotic arm 1 of the present invention, the both end oblique sections of the sleeve 111 of the concatenated robotic arm segment 11 and the front end oblique section 1111 of the sleeve 111' of the terminal robotic arm segment 12 are a circle with the same diameter, so that after the concatenated robotic arm segment 11 and/or the terminal robotic arm segment 12 of the present invention is concatenated in series, the concatenated robotic arm segments 11 and/or the terminal robotic arm segments 12 concatenated in series can completely perform relative rotations of up to 360 degrees along the adjacent oblique sections of the two concatenated of the robotic arm segments without extra volume. In addition, since the hollow structure penetrating both ends of the concatenated robotic arm segment 11 and/or the terminal robotic arm segment 12 takes the rotation center of the pivoting structure as the center point of itself, objects placed in the hollow structure would not be affected when the concatenated robotic arm segment 11 and/or the terminal robotic arm segment 12 concatenated in series perform relative rotational movement.

Furthermore, in the multi-segment rotation robotic arm 1 of the present invention, each concatenated robotic arm segment 11 and/or the terminal robotic arm segment 12 of the robotic arm is concatenated in series with the conductive ring combination 11321, so that it is only necessary to connect an external electric supply to the terminal robotic arm segment 12 of the multi-segment rotation robotic arm 1 of the present invention for supplying electricity to the entire multi-segment rotation robotic arm 1; and since the conductive ring combination 11321 is a circular metal ring, after the concatenated robotic arm segments 11 and/or the terminal robotic arm segments 12 are concatenated in series, the two robotic arm segments connected in series can freely rotate 360 degrees without affecting the conduction of electricity; or, each of the concatenated robotic arm segments 11 and/or the terminal robotic arm segments 12 concatenated in series has a battery to independently provide electricity for a single concatenated robotic arm segment 11 and/or the terminal robotic arm segment 12, so that the rotation of the concatenated robotic arm segment 11 would not affect the conduction of electricity.

In addition, in the multi-segment rotation robotic arm 1 of the present invention, each concatenated robotic arm segment 11 and/or the terminal robotic arm segment 12 comprises the independent signal receiving module 114 and the signal processing module 115, and terminal the robotic arm segment 12 can further comprises the instrument device 116, so that each concatenated robotic arm segment 11 and/or the terminal robotic arm segment 12 can be independently controlled to reduce each controlled unit and to improve the overall mobility and accuracy of the multi-segment rotation robotic arm 1 of the present invention.

Therefore, the multi-segment rotation robotic arm 1 of the present invention can arbitrarily concatenate a plurality of the concatenated robotic arm segments 11 of the present invention in series according to the use requirements, and the concatenating way of the concatenated robotic arm segments 11 and/or the terminal robotic arm segments 12 enables them to rotate 360 degrees along the oblique section of each other when they rotate relatively to each other, and the electric supply will not be affected by the rotation at all, so as to overcome the limitation of the joint rotation angle of the conventional robotic arm in the art of the present invention, and to reduce the volume increase by rotated joints, so the multi-segment rotation robotic arm 1 of the present invention can be more effectively used in minimally invasive surgery with limited space configuration. Specifically, the multi-segment rotation robotic arm 1 of the present invention can effectively adapt to the complex and tortuous space in the body cavity to reduce the possibility of expanding the opening of the minimally invasive surgery and causing damage to organs or tissues in the body cavity. Moreover, because each concatenated robotic arm segment 11 and/or the terminal robotic arm segment 12 of the multi-segment rotation robotic arm of the present invention can be independently controlled, this method of reducing the control unit enables the multi-segment rotation robotic arm 1 of the present invention to adapt to the environment in terms of mobility and accuracy.

What is claimed is:
1. A multi-segment rotation robotic arm, comprising:
a plurality of concatenated robotic arm segments; and
a pivoting structure and a driving device are located between two of the concatenated robotic arm segments, wherein, the pivoting structure is located between an adjacent oblique section of the two of the concatenated robotic arm segments, and the driving device is used to drive the pivoting structure so that the two of the concatenated robotic arm segments move relatively to each other along the adjacent oblique section, characterized by:
any one of the concatenated robotic arm segments is an elliptical cylinder having an oblique section at each end, and the oblique section is a circle, a circular flange is formed on the rear end oblique section, and a circular groove is formed on the front end oblique section, when the front end oblique section and the rear end oblique section are adjacent to each other, the circular flange and the circular groove cooperate with each other;
wherein the driving device comprises:
an electric motor; and
an electrical conductive element electrically connected to the motor, the electrical conductive element comprises a conductive ring combination and a conductive wire combination, the conductive ring combination is arranged on the circular flange and the circular groove of the concatenated robotic arm segment respectively, and the electrical conductive wire combination electrically connected between the conductive ring combination and the electric motor; and
wherein the pivoting structure comprises:
a front end joint, which is near the front end oblique section; and
a rear end joint, which is near the rear end oblique section of the next concatenated robotic arm segment,
wherein the front end joint and the rear end joint are pivotally coupled by a universal joint.

2. The multi-segment rotation robotic arm according to claim 1, wherein the elliptical cylinder of the robotic arm segment has at least one hollow structure which penetrates both ends of the robotic arm segment.

3. The multi-segment rotation robotic arm according to claim 2, wherein the driving device further comprises: a battery for providing electricity to the electric motor; wherein, the electric motor is installed at one end of two of the concatenated robotic arm segments for driving the pivoting structure, and the electrical conductive element or the battery is arranged in the hollow structure.

4. The multi-segment rotation robotic arm according to claim 3, wherein the conductive ring combination is arranged at the adjacent oblique section of the two of the concatenated robotic arm segments, so that the electrical conduction element of the concatenated robotic arm segments is electrically connected by the conductive ring combination to conduct electricity.

5. The multi-segment rotation robotic arm according to claim 1, wherein the driving device further comprises a signal receiving module and a signal processing module; wherein, the signal processing module is electrically connected to the signal receiving module and the electric motor.

6. The multi-segment rotation robotic arm according to claim 5, wherein the signal receiving module receives a control signal and transmits the control signal to the signal processing module, and the signal processing module receives the control signal to calculate a rotation angle.

7. The multi-segment rotation robotic arm according to claim 6, wherein the signal processing module controls the rotation of the electric motor according to the rotation angle and drives two of the concatenated robotic arm segments to perform relative rotation at the rotation angle along the adjacent oblique sections.

8. The multi-segment rotation robotic arm according to claim 1, further comprising a terminal robotic arm segment;
    wherein the terminal robotic arm segment comprises:
        a signal receiving module;
        an instrument device; and
        a signal processing module;
    wherein the signal processing module is electrically connected to the signal receiving module and the instrument device.

9. The multi-segment rotation robotic arm according to claim 8, wherein the signal receiving module receives a control signal and transmits the control signal to the signal processing module, and the signal processing module receives the control signal to generate an operation instruction.

10. The multi-segment rotation robotic arm according to claim 9, wherein the signal processing module controls an operation of the instrument device according to the operation instruction.

* * * * *